(12) United States Patent
Keller et al.

(10) Patent No.: US 7,836,777 B2
(45) Date of Patent: Nov. 23, 2010

(54) COMPOSITE GLAZING WITH AN INCREASE ENERGY ABSORPTION AND FILM INTERLAYERS THAT ARE SUITABLE FOR SAID GLAZING

(75) Inventors: Uwe Keller, Bonn (DE); Martin Londschien, Troisdorf (DE)

(73) Assignee: Kuraray Europe GmbH, Frankfurt (DE)

( * ) Notice: Subject to any disclaimer, the term of this patent is extended or adjusted under 35 U.S.C. 154(b) by 334 days.

(21) Appl. No.: 11/720,019

(22) PCT Filed: Nov. 22, 2005

(86) PCT No.: PCT/EP2005/056136

§ 371 (c)(1),
(2), (4) Date: Oct. 24, 2008

(87) PCT Pub. No.: WO2006/056568

PCT Pub. Date: Jun. 1, 2006

(65) Prior Publication Data

US 2009/0229371 A1   Sep. 17, 2009

(30) Foreign Application Priority Data

Nov. 23, 2004   (DE) ................ 10 2004 000 053

(51) Int. Cl.
*G01L 9/04* (2006.01)
(52) U.S. Cl. .......................................... 73/826; 73/860
(58) Field of Classification Search ............ 73/760–826
See application file for complete search history.

(56) References Cited

U.S. PATENT DOCUMENTS

| 3,762,988 | A |   | 10/1973 | Clock et al. |
| 4,041,208 | A |   | 8/1977 | Seeger et al. |
| 4,361,625 | A |   | 11/1982 | Beckmann et al. |
| 4,822,684 | A |   | 4/1989 | Hotta et al. |
| 5,309,767 | A | * | 5/1994 | Parmar et al. ................. 73/705 |
| 5,340,654 | A |   | 8/1994 | Ueda et al. |
| 6,368,730 | B1 | * | 4/2002 | Kishimoto et al. .......... 428/690 |
| 7,113,472 | B2 | * | 9/2006 | Wada et al. ............ 369/112.18 |
| 7,197,941 | B2 |   | 4/2007 | Nugue et al. |
| 2001/0048495 | A1 | * | 12/2001 | Yamaguchi et al. ......... 349/113 |
| 2004/0052937 | A1 | * | 3/2004 | Ito et al. ..................... 427/162 |
| 2005/0249959 | A1 |   | 11/2005 | Okamoto et al. |
| 2006/0070694 | A1 |   | 4/2006 | Rehfeld et al. |

FOREIGN PATENT DOCUMENTS

DE   197 56 274 A1   6/1999

(Continued)

*Primary Examiner*—Max Noori
(74) *Attorney, Agent, or Firm*—Millen, White, Zelano & Branigan, P.C.

(57) ABSTRACT

The present invention relates to a safety composite system, and/or intermediate layer films suitable for therein, having a high penetration resistance, i.e., energy absorption on sudden mechanical stress and to a process for the determination of the maximum energy absorption of intermediate layer films on sudden mechanical stress. The thickness-dependent energy absorption E [J/mm] of at least one film is determined according to DIN EN ISO 8256 on a test specimen of the safety composite system provided with pre-broken transparent panels and amounts to at least E>d−b, d being the film thickness and b being a constant. The safety composite system can be used in particular for the manufacture of composite glazings.

18 Claims, 3 Drawing Sheets

FOREIGN PATENT DOCUMENTS

| | | |
|---|---|---|
| EP | 1 151 855 A | 11/2001 |
| EP | 1 452 308 A | 9/2004 |
| EP | 1 591 234 A | 11/2005 |
| GB | 1 221 285 A | 2/1971 |
| GB | 1 260 213 A | 1/1972 |
| WO | WO 99/58334 A | 11/1999 |
| WO | WO 01/43963 A | 6/2001 |
| WO | WO 03/087785 A | 10/2003 |

* cited by examiner

COMPOSITE GLAZING WITH AN INCREASE ENERGY ABSORPTION AND FILM INTERLAYERS THAT ARE SUITABLE FOR SAID GLAZING

The present invention relates to composite glazing and/or intermediate layer films suitable for it having a high resistance to penetration, i.e. energy absorption on sudden mechanical stress, and to a process for the determination of the maximum energy absorption by intermediate layer films on sudden mechanical stress.

TECHNICAL FIELD

As is well known, the fracture behaviour of composite materials such as composite safety glass (CSG) with an intermediate layer of polyvinyl butyral film (PVB film) depends on the adhesion between the film and the glass. If the adhesion is very strong, it ensures, in the case of mechanical failure of the composite glass e.g. as a result of the effect of an impact, that the broken pieces of glass continue to adhere to the film so that sharp-edged glass fragments cannot detach themselves. On the other hand, an impinging object can penetrate through the composite glass relatively easily since the PBV film adheres so strongly to the glass that it is unable to detach itself from the glass at the site of impact and able to undergo hardly any elastic deformation and consequently contributes only little to slowing down the object. If the adhesion to the glass is at a low level the PBV film is able to detach itself from the glass at the site of impact under strain and become deformed as a result of which the impinging object is slowed down.

Since, on the other hand, too low an adhesion facilitates glass fragments detaching themselves from the PVB film and consequently increases the risk of injury to persons, attempts are being made in practice to find a compromise solution between high and low adhesion, i.e. a medium adhesion level in order to achieve fragment bonding at a level which is as high as possible.

It is common practice to provide proof of the mechanical impact resistance or, more accurately, the penetration resistance of composite safety glass by way of the impact of steel balls which are dropped from a defined height onto a test pane secured vertically and which consequently have a defined kinetic energy. If the kinetic energy of CSG can be absorbed completely, the steel ball is caught; otherwise, the ball passes through the composite. The falling ball test forms a central part of national and international industrial standards, the weight of the ball, the dimensions of the test panes to be used, the test temperature, the height of drop and other experimental details being laid down precisely in order to arrive at a classification of composite glass structures on the basis of their impact resistance. According to the European rule ECE-R 43 for the official approval of composite safety glass as windscreen in motor vehicles, for example, proof of penetration resistance at a drop height of at least 4 m using a steel ball of 2.26 kg at a temperature of 23° C. must be provided. For CSG in building applications, the European Standard EN 356 specifies protection classes P1, P2 and P3, for example, which require resistance to penetration by three steel balls of a weight of 4 kg dropped in succession from different drop heights.

STATE OF THE ART

Being a destructive test method, however, the falling ball test is a method with a high level of material consumption since several test panes are used up for the determination of a reliable value. Moreover, in the case of a fairly large pane format, in particular, the result depends strongly on the degree of toughening and/or the orientation of standard float glass which exhibits unequal surfaces attributable to the manufacturing process. An accurate measurement of the energy and consequently drawing conclusions regarding the energy absorption by the film, based on a standard-sized fracture length, is not possible means of the falling ball test.

Although the connection between glass adhesion and penetration resistance is empirically well established for SCG with a PVB film, it is not possible to draw reliable conclusions on the basis of a measured adhesion level as such regarding the impact resistance of composite glazing. Although attempts have been made to arrive at an improved model (WO 03/087785 A2) by combining an adhesion measurement with a mechanical property to be determined on the intermediate layer, its predictive value is limited by the fact that the film strength relevant in the case of an impact event is not taken into consideration under dynamic conditions.

OBJECT OF THE INVENTION

The energy absorption capacity of composite glazing on impact of an object is determined by the following factors: on impact, the object destroys the glass panes bonded together by the intermediate layer and, depending on the geometry of the object, forms an indentation or a creator forcing a local deviation of the film from the original plane to occur which is necessarily accompanied by an expansion of the film. As a result of the critical energy of the object, the intermediate film is expanded, begins to detach itself from the glass panes and to partially escape from between the glass fragments. The penetration resistance of the composite glazing known in the state of the art is worthy of improvement in view of the increased safety requirements in the motor vehicle and architectural sector as well as the increased use of large glass surfaces. It was consequently the project of the present invention to make particularly penetration resistant composite systems available.

DESCRIPTION OF THE INVENTION

The subject matter of the present invention consequently consists of safety composite systems consisting of at least two transparent panels of glass and at least one film based on partially acetalized polyvinyl alcohol which is arranged between the panels, at least one film having a specific thickness-dependent energy absorption E [J/mm] of E>d−b determined on a test specimen consisting of the safety composite system provided with previously broken transparent panels according to DIN EN ISO 8256 (2004), the film thickness d amounting to 0.01 to 25 mm, the width of the test body to 14 mm and the constant b to 0.275 to −0.275, with the proviso that d=0.375 for film thicknesses of less 0.375 mm.

Measuring of the energy absorption of the film preferably takes place by way of the process according to the invention described in the following. By means of this process it is possible to determine the total energy absorption of an intermediate layer film in a laminate, i.e. the expansion and delamination of the film under suddenly occurring mechanical stresses.

Penetration-resistant composite systems according to the meaning of the present invention are consequently equipped not only with particularly tear-resistant intermediate layer films but also exhibit a balanced adhesion of these films to the cover material, i.e. a certain delamination tendency. The energy consumed by delamination is a measure of the adhesion of the film under the effect of a dynamic force. If the adhesion is too low only little energy is consumed by delamination; if the adhesion is too high, the film will tear rather than delaminate such that only little energy is consumed also in this case. The consequence in the case of an excessive adhesion is, even with extremely tear-resistant films, is a rapid penetration since the film breaks at the edges of fracture of the glass.

The maximum energy absorption of the film determined via the tensile impact strength depends on the width and the thickness d [mm] of the film. Films according to the invention exhibit an energy absorption E in J/mm of E>d−b with a width of the test specimen of 14 mm; the energy absorption is thus based merely on the crack width and not on the cross-section of the film.

The constant b for the determination of the energy absorption of the films usable according to the invention consequently amounts to preferably 0.275; 0.250; 0.225; 0.200; 0.175; 0.150; 0.125; 0.100; 0.075; 0.050; 0.025; 0.000; −0.025; −0.050; −0.075; −0.100; −0.125; −0.150; −0.175; −0.200; −0.225; −0.250 or 0.275 and/or it can be within the range between two of these values (e.g. −0.75 to 0.75).

BRIEF DESCRIPTION OF THE DRAWINGS

FIG. 1 preferably shows a minimal energy absorption of films usable according to the invention as a function of their thickness. The bottom straight line represents films with a constant b=0.25; the middle straight line represents b=0.25 and the upper straight line b=0.20. The energy absorption of films usable according to the invention is above the straight lines concerned. For film thicknesses of less than 0.375 mm, d is assumed to be equal 0.375, irrespective of the thickness, i.e. the energy absorption of films of this thickness depends only on the constant b.

Figure 1:
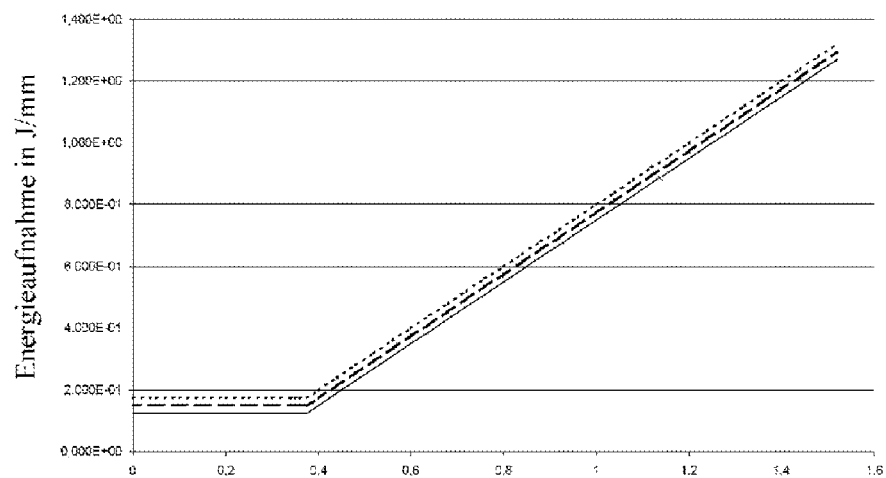
FIG. 1 illustrates minimal energy absorption of films usable according to the invention as a function of their thickness.

The films preferably have thicknesses, common for composite glazing, of 0.38 mm, 0.76 mm, 1.14, 1.52 mm or integer multiples of 0.38 mm. The following tables show the preferred energy absorption values of at least one film of the safety composite system according to the invention with the above-mentioned thicknesses of the films:

| Thickness of the film [mm] | min. energy absorption [J/mm] |
| --- | --- |
| 0.38 | 0.10 preferably 0.12; 0.15 or 0.20 |
| 0.76 | 0.50 preferably 0.55; 0.60 or 0.65 |
| 1.14 | 0.90 preferably 1.00; 1.10 or 1.20 |
| 1.52 | 1.30 preferably 1.40; 1.60 or 1.80 |

The value of 10 J/mm$^2$ can be given as being the upper limit of the energy absorption of these films, based on the cross-section (i.e. the width and thickness of the film).

The transparent panels used are preferably those of glass, polycarbonate or polymethyl methacrylate (PMMA). Insofar as both panels consist of glass, the present invention relates to a composite safety glass with a particularly high penetration resistance.

Apart from the energy absorption of the films, the composite safety systems according to the invention can be additionally characterised by the adhesion of the film to the transparent panels. Thus, the adhesion, determined by the compression shear test according to DE 19 756 274 A1, of at least one film to a glass surface is preferably 8 to 30 N/mm$^2$.

The safety composite systems according to the invention, in particular the composite safety glass in this case, are produced in the usual manner known to the expert by laminating the transparent panels with at least one film under elevated or reduced pressure and at an elevated temperature. Processes suitable for this purpose are disclosed e.g. in EP 1 235 683 B1 or EP 1 181 258 B1.

Intermediate layer films used according to the invention are based on partially acetalized polyvinyl alcohols, in this case in particular polyvinyl butyral (PVB). PVB can be used in the non-crosslinked or crosslinked state, e.g. with dialdehydes or aldehyde carboxylic acids according to DE 10 143 109 A1 or WO 02/40578 A1. Intermediate layer films based on partially acetalized polyvinyl alcohol contain, apart from light stabilisers and adhesion regulators, usually between 20 and 35% of plasticisers such as e.g. 3G8 or dihexyl adipate. Systems of this type are described e.g. in EP 0 185 863 A1, WO 03/097347 A1 and WO 01/43963 A1. The use of at least one film based on crosslinked or non-cross linked, plasticiser-containing polyvinyl butyral is preferred.

In a further variation of the invention, at least one intermediate layer film consists of several partial layers, based on the materials of partially acetalized polyvinyl alcohol, polyethylene terephthalate (PET), polyurethane (PU), polymethyl methacrylate (PMMA) or polyolefins respectively. 2, 3, 4 or more partial films of different materials can be used. In a particularly preferred variation of the invention, a thin film of another material is embedded between two outer films based on partially acetalized polyvinyl alcohol. Films of PET approx. 30 bi 500 μm thick have proved suitable for this purpose.

It is also possible for several partial films based exclusively on partially acetalized polyvinyl alcohol to be combined. Such film laminates are known e.g. from EP 1 218 690 A1, JP 2004-99354 or DE 10 200 400 0023 and are produced by coextrusion or co-lamination of corresponding partial films. These partial films differ from each other regarding their polymeric material, their molecular weight or the type and quantity of plasticiser and, in the case of PVB, additionally by their degree of acetylation or residual alcohol content.

Films used according to the invention preferably exhibit at least two partial films of crosslinked or non-crosslinked polyvinyl butyral with different plasticiser contents. In this case, the use of three partial films is preferred, one hard partial film with a low plasticiser content being encapsulated by two soft partial films with higher plasticiser contents.

Composite safety systems according to the invention may exhibit 2 to 10 transparent panels and correspondingly 1 to 9 intermediate layer films which may optionally in turn be built up of partial films. Appropriately, all the intermediate layer films used have the above-mentioned energy absorption; however, it is also possible for commercial films, e.g. those based on plasticiser-containing polyvinyl butyral according to WO 03/051974 A1 or EP 1 412 178 B1 to be used, apart from films with the energy absorption according to the invention.

Films used according to the invention may additionally exhibit a cold crack temperature according to ISO 8570 of less than −35° C. Such films have a low tendency to brittle failure and consequently improved safety properties at low temperatures even at low temperatures such as those frequently occurring e.g. in the case of aeroplanes during flight.

Measuring of the energy absorption of the film can take place by means of the process according to the invention, i.e. a pre-broken glass laminate. However, it is also possible to determine the tensile impact strength of the films themselves, i.e. without lamination with transparent panels, according to DIN ISO 8256. Films which are particularly suitable for the composite system according to the invention exhibit an energy absorption, determined according to this standard, of more than 2000 kJ/m². The value of 10,000 kJ/m² can be given as the upper limit of the energy absorption of these films, based on the cross-section (i.e. width times thickness of the film).

The difference between the values determined on the film and the values determined by the process according to the invention on the laminate is obtained from the missing delamination work and the greater expansion surface of the film since, in the laminate test, the expansion of the film takes place only in the delamination area.

The systems according to the invention can replace commercial composite safety glass as composite glazing with two glass panes and an intermediate layer film, e.g. as motor vehicle windscreen. In the case of increased safety requirements, composite systems with more than two glass panes and at least two intermediate layer films can be used. Composites with 4 or more glass panes and correspondingly 3 and more intermediate layer films are referred to as bullet-proof glass.

Composite safety systems according to the invention are preferably used as glazing or facade material in the architectural sector, hurricane resistant glazing, glazing resistant to penetration by thrown objects and to penetration through break-through, glazing in the aeroplane or motor vehicle sector, glazing in the above head sector or as stair treads.

A further object of the present invention is a process for measuring the tensile impact strength of laminates of two transparent panels and one film arranged between the panels. The energy absorption is determined by the transparent panels being pre-broken in such a way that the edges of the fractures facing the intermediate layer are not displaced vis-à-vis each other. Care should be taken when preparing the specimens to ensure that the intermediate layer film is not stretched or delaminated during pre-breaking of the transparent panels.

Figure 2:
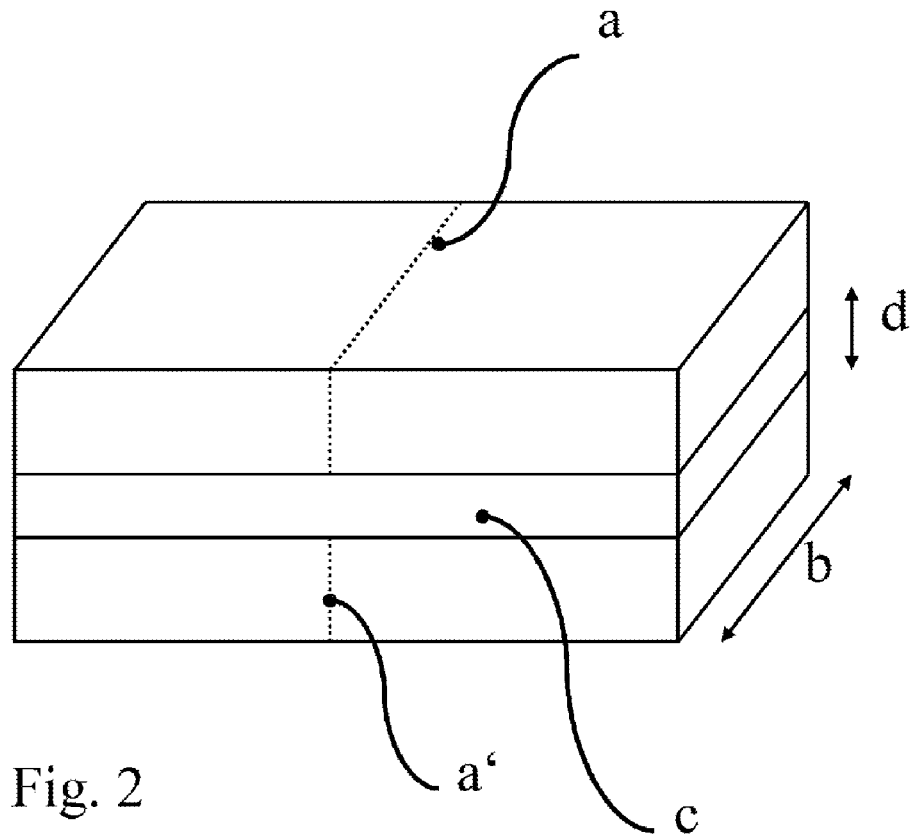
FIG. 2 illustrates a test specimen having transparent panels a and a' and intermediate layer film c.

FIG. 2 shows such a test specimen in which a and a' indicate the pre-broken transparent panels and c the intermediate layer film. The references b and d represent the width and/or thickness of the film. Subsequently, a defined load is applied by means of a tensile impact machine (compare FIGS. 3 and 4) and the energy absorption is determined according to DIN ISO 8256.

The invention consequently relates to a method for directly measuring that energy which directly describes the performance e.g. of a composite safety glass in the case of a dynamic impact event. The method consequently provides the possibility of optimising intermediate layers regarding their performance in the case of dynamic impact events and to select them with a view to dynamic impact events. An advantage of the method consequently consists in that no adhesion tests need to be carried out on the laminate or mechanical measurements on the intermediate layer but, instead, the energy absorption on impact-type stress can be measured in a direct test on test specimens cut out from the composite safety glass. The mechanism of energy absorption and dissipation which neutralises the kinetic energy of an impinging object, e.g. a steel ball thrown for test purposes, to such an extent that the object does not penetrate through the composite safety glass consists essentially of the intermediate layer detaching itself from the glass under the suddenly occurring tensile stress, for which energy has to be applied. To monitor the sudden tensile stress, the method according to the invention uses the equipment described in DIN EN ISO 8256 (2004) (diagrammatic representation in FIGS. 3 and 4) for the execution of the tensile impact test. The test is carried out in deviation from the known plastics test on laminate strips in which the two glass layers are partially broken in the middle and without displacement.

Figure 3:
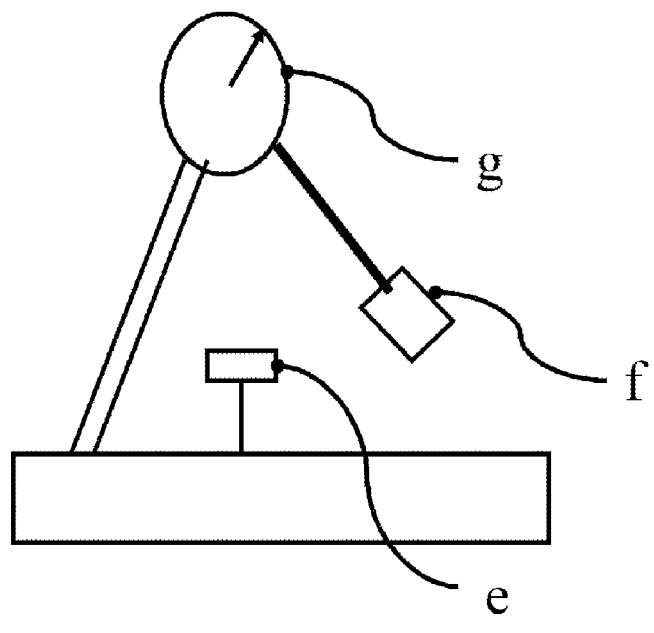
FIG. 3 illustrates the equipment used in the execution of the tensile impact test wherein e) represents a fixed specimen, f) represents the impact tool fixed to a pendulum, and g) represents the pendulum retainer.
Figure 4:
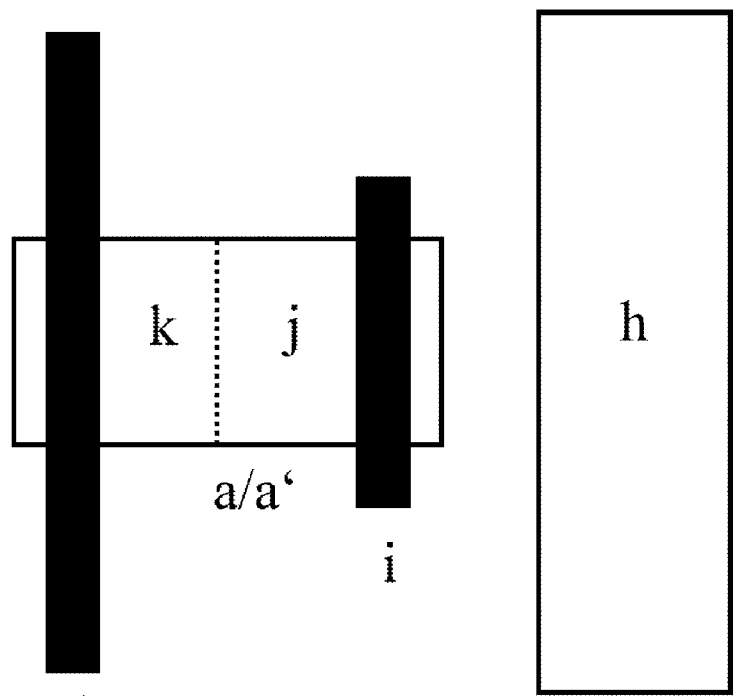
FIG. 4 shows the yoke-shaped impact tool h which impacts onto a specimen carrier 1 in the direction of the arrow and smashes the specimen at the fracture site a/a into the partial fragments k and j.

In FIG. 3, the equipment used in the process according to the invention is shown as a drawing, e) representing the fixed specimen, f) the impact tool fixed to a pendulum and g) the pendulum retainer and/or the measuring equipment. The impact tool f) is adjusted to the maximum deflection of the pendulum, released and then impacts onto to the specimen at the bottom peak of the pendulum. This defined kinetic energy smashes the specimen and the energy required for this is determined according to DIN ISO 8256. FIG. 4 shows the yoke-shaped impact tool h which impacts onto the specimen carrier l in the direction of the arrow and smashes the specimen at the fracture site a/a into the partial fragments k and j. The partial fragment j is firmly connected to the retaining device i and remains in the equipment; the partial fragment k and the carrier l are projected away in the direction of the arrow. By way of the width of the film to be determined on the laminate strip, the amount of work performed is converted to energy absorption per width. Regarding the calculation and the exact method of operation, reference should be made to DIN ISO 8256 (2004).

Preparation for the Measurement of the Tensile Impact Resistance

The laminate test pieces are cut to a width of 14.0±1.0 mm and a length of 80.0±1.0 mm from a CSG which consists of two float glass panes with a thickness of 2.0±0.1 mm and the intermediate layer. In order to avoid falsification of the results, care should be taken to ensure that the fracture edges touching the intermediate layer of the opposing glass layers are situated in a joint plane oriented vertically to the main axis of the laminate test piece with a tolerance of ±0.5 mm, i.e. exhibit no reciprocal displacement (compare FIG. 2; a/a'). The laminate had previously been produced in a manner known to the expert.

In order to obtain a meaningful value for the energy absorption of a material, 15 test specimens are cut out from a CSG pane, their tensile impact resistance is determined and the average value calculated from the individual values. In a manner which differs from the plastics test on homogeneous material described by DIN EN ISO 8256, the tensile impact resistance of the laminate test specimens is not related to their cross-section and expressed in kK/m² but to the film width determined on individual test specimens in mm within the set framework of 14.0±1.0 mm. The energy absorption is consequently expressed in the unit of J/mm. Moreover, the procedure is, as far as possible and physically meaningful, that according to the above-mentioned test standard DIN EN ISO 8256 in the version valid since 2004. With respect to the test machine, reference should be made to ISO 13802.

Naturally, the method is valid irrespective of whether the intermediate layer material is composed of an individual homogeneous layer or has a complex composition, i.e. consists of a sequence of two or more different layers or functional layers.

It is possible to achieve a CSG with an energy absorption of 0.40 J/mm measured as described above by means of commercial, adhesion-reducing PVB films of a thickness of 0.76 mm. The pummel adhesion of such films to the float glass must be within the region of 2 to 4. Since films for the manufacture of CSG usually have a structured surface, the strength of the intermediate layer can be determined reliably by determining the mass per surface area in combination with the physical density.

Tensile Compression Test According to DE 197 56 274 A1

Figure 5:
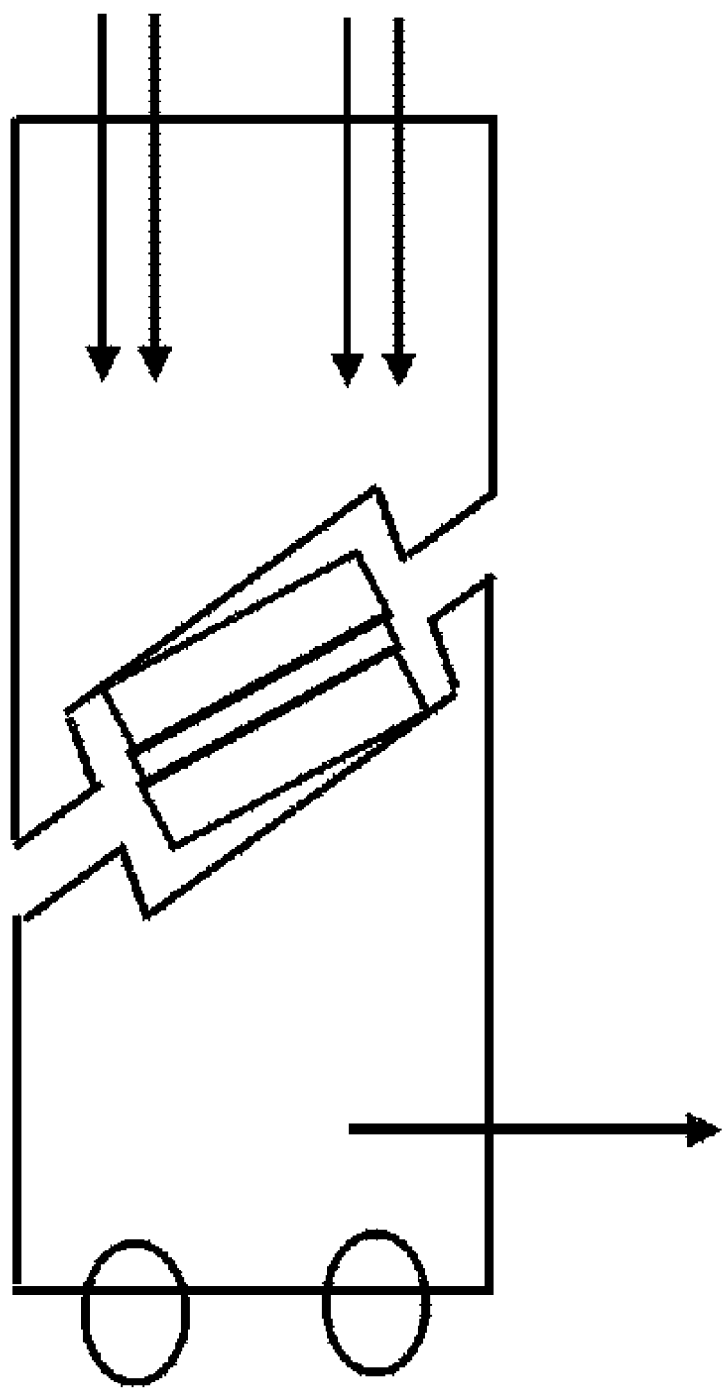
FIG. 5 illustrates the equipment used in a tensile compression test.

To assess the adhesion of a PVB film to mineral glass, a so-called compression shear test is carried out according to the following description. To make the test specimen, the PVB adhesive film to be tested is introduced between two level silicate glass panes of size 300 mm×300 mm with a thickness of 4 mm, deaerated in a pre-composite oven with calendar rollers to form a glass precomposite and subsequently pressed in an autoclave at a pressure of 12 bar and at a temperature of 140° C. within 30 min to form a level composite safety glass. 10 specimens measuring 25.4 mm×25.4 mm are cut out from the composite safety glass thus produced. These specimens are clamped at an angle of 45° into a two-part test apparatus shown symbolically in FIG. 5. The upper half is subjected to a continuously rising force directed accurately vertically downwards until a shearing effect occurs within the test specimen, i.e. the composite safety glass pane to be tested.

The test parameters are as follows:

| | |
|---|---|
| Test specimen | square 25.4 mm × 25.4 mm |
| Laying | bottom pane with the air side or fire side turned towards the film (air/air) or upper and bottom pane with the tin side turned towards the film (bath/bath) |
| Storage before the test | for 4 h in a standard climate of 23° C./50% rh |
| Advance: | 2.5 mm/min |
| Number of specimens: | 10 |
| Evaluation: | maximum force required to shear off the film from the glass. The force is based on the specimen surface (N/mm² or psi) |

For every example, the force exerted during shearing off on ten equal test specimens is determined in a linear manner. Insofar as reference is made in the following examples and the claims to the average compression shear test value, it refers to this average value from 10 measurements.

EXAMPLES

Comparative Example 1

A composite safety glass measuring 30×30 cm is produced from the product TROSIFOL® MB 0.76 (HT TROPLAST AG) and 2 pieces of float glass with a thickness of 2 mm (Optifloat® from Pilkington). From this film and Optifloat® with a thickness of 4 mm, 6 test panes measuring 90×110 cm are laminated. From the CSG with the construction of 2 mm glass/0.76 mm film/2 mm glass, 15 laminate test pieces measuring 80×14 mm are cut for which purpose the glass is first scratched with a diamond glass cutter, prebroken along the scratched intended fracture points by minimal bending and the film is cut through using a razor blade. In this connection, care should be taken to ensure that the intermediate layer is subjected to such little strain as is just required for access by the razor blade. The laminate test pieces are scratched on both sides by means of the diamond glasscutter in the centre and prebroken by minimum bending. Should, in this case, the fracture edge of the cracks extending to the intermediate layer be displaced vis-à-vis each other by more than 0.5 mm, these laminate test pieces must be replaced. For protection against becoming damp, the laminate test pieces are sealed in bags of aluminium-coated PE. Before the test on the tensile impact apparatus, the test specimens are bonded on both ends with a layer of a commercial adhesive tape (e.g. tesa-Film type 5740), in order to prevent the test specimens from sliding out from between the clamping jaws during the test. The CSG which contains the intermediate layer material TROSIFOL MB with a thickness of 0.76 mm reaches, during the test on the tensile impact apparatus, a mean value of energy absorption of 0.066 J/mm. During the test according to EN 356, the CSG-4 mm glass/0.76 mm film/4 mm-passes the test for class P1 but fails class P2 test.

Comparative Example 2

A composite safety glass measuring 30×30 cm is produced from the product Butacite® B5 with a thickness of 0.76 mm (Du Pont) and 2 pieces of float glass with a thickness of 2 mm (Optifloat® from Pilkington). From the same film and Optifloat® with a thickness of 4 mm, 6 test panes measuring 90×110 cm are laminated. From the CSG with the construction of 2 mm glass/0.76 mm film/2 mm glass, 15 laminate test pieces measuring 80×14 mm are cut. The CSG which contains the intermediate layer material Butacite® B5 with a thickness of 0.76 mm reaches, during the test on the tensile impact apparatus, a mean value of energy absorption of 0.114 J/mm. During the test according to EN 356, the CSG—4 mm glass/0.76 mm film/4 mm—passes the test for class P1 but 2 out of 3 panes fail in the case of a drop height of 3 m (class P2).

Comparative Example 3

A composite safety glass measuring 30×30 cm is produced from the product Saflex® RB 41 with a thickness of 0.76 mm (Solutia) and 2 pieces of float glass with a thickness of 2 mm (Optifloat® from Pilkington). From the same film and Optifloat® with a thickness of 4 mm, 6 test panes measuring 90×110 cm are laminated. From the CSG with the construction of 2 mm glass/0.76 mm film/2 mm glass, 15 laminate test pieces measuring 80×14 mm are cut. The CSG which contains the intermediate layer material Saflex® RB 41 with a thickness of 0.76 mm reaches, during the test on the tensile impact apparatus, a mean value of energy absorption of 0.210 J/mm. During the test according to EN 356, the CSG—4 mm glass/0.76 mm film/4 mm—passes the test for class P1 and P2, although in the case of one of the three panes tested for P2, the third ball almost penetrates through since a crack in the film occurred.

Comparative Example 4

A composite safety glass measuring 30×30 cm is produced from the product TROSIFOL® MV 0.76 mm (HT TROPLAST AG) and 2 pieces of float glass with a thickness of 2 mm (Optifloat® from Pilkington). From the same film and Optifloat® with a thickness of 4 mm, 6 test panes measuring 90×110 cm are laminated. From the CSG with the construction of 2 mm glass/0.76 mm film/2 mm glass, 15 laminate test pieces measuring 80×14 mm are cut. The CSG which contains the intermediate layer material TROSIFOL® MV 0.76 reaches, during the test on the tensile impact apparatus, a mean value of energy absorption of 0.380 J/mm. During the test according to EN 356, the CSG—4 mm glass/0.76 mm film/4 mm—passes the test for classes P1 and P2 safely.

Examples 1-4 According to the Invention

Flat films with the compositions indicated in Table 1 were produced in a thickness of 0.76 mm in an extrusion facility equipped with a slit die, while the temperature of the mass in the extruder was not more than 210° C. Using these films and two pieces of float glass in a thickness of 2 mm (Optifloat® from Pilkington), pieces of composite safety glass measuring 30×30 cm were produced. From the same films and Optifloat® with a thickness of 4 mm, 6 test panes measuring 90×110 cm are laminated. From the CSG with the construction of 2 mm glass/0.76 mm film/2 mm glass, 15 laminate test pieces measuring 80×14 mm are cut. The CSG which contains the intermediate layer materials with the thickness of 0.76 reaches, during the test on the tensile impact apparatus, the mean value of energy absorption indicated in Table 1. During the test according to EN 356, the CSG—4 mm glass/0.76 mm mm—passed the test with a height of drop, increased by 0.5 m, of 3.5 m (class P1+0.5 m) in the case of 3 out of 3 panes.

TABLE 1

|  | Example 1 | Example 2 | Example 3 | Example 4 |
|---|---|---|---|---|
| PVB | 73 | 73 | 73 | 73 |
| PVOH content | 20.0 | 20.0 | 20.0 | 20.0 |
| 3G8 | 22.5 | 19.5 | 19.5 | 19.5 |
| DBEEA | 4.5 | 7.5 | — | — |
| DBEA | — | — | 7.5 | — |
| DBES | — | — | — | 7.5 |
| Tinuvin 328 | 0.15 | 0.15 | 0.15 | 0.15 |
| KAc | 0.005 | 0.005 | 0.005 | 0.005 |
| $MgAc_2*4H_2O$ | 0.0052 | 0.0052 | 0.0052 | 0.0052 |
| Energy absorption | 0.51 J/mm | 0.49 J/mm | 0.51 J/mm | 0.55 J/mm |
| Cold crack temperature | −44° C. | −41° C. | −41° C. | −43° C. |
| Tensile impact resistance | 1940 $kJ/m^2$ | 1933 $kJ/m^2$ | 2100 $kJ/m^2$ | 2185 $kJ/m^2$ |

All quantity values in % by weight, PVOH=polyvinyl alcohol content of the PVB resin in % by weight. The quantity values of the additives relate to 100% by weight of the basic mixture. 3G8=triethylene glycol-bis-2-ethyl hexanoat. DBEEA=di(butoxyethyl) adipate. Ac=acetate residue.

The invention claimed is:

1. A safety composite system comprising: at least two transparent panels and at least one film based on partially acetalized polyvinyl alcohol which is arranged between the panels,
    wherein at least one film has a specific thickness-dependent energy absorption E [J/mm] of E>d−b determined on a test specimen consisting of the safety composite system provided with previously broken transparent panels according to DIN EN ISO 8256, the film thickness d amounting to 0.01 to 25 mm, the width of the test body to 14 mm and the constant b to 0.275 to −0.275, with the proviso that d=0.375 for film thicknesses of less 0.375 mm, and
    wherein at least one film is based on crosslinked or non-crosslinked plasticiser-containing polyvinyl butyral.

2. A safety composite system according to claim 1, wherein at least one film consists of several partial layers based on the materials of partially acetalized polyvinyl alcohol, PET, PU, PMMA and/or polyolefin.

3. A safety composite system according to claim 1, wherein said composite contains at least two films of crosslinked or non-crosslinked polyvinyl butyral with different plasticiser contents.

4. A safety composite system according to claim 1, wherein at least one film consists of at least two partial films of crosslinked or non-crosslinked polyvinyl butyral with different plasticiser contents.

5. A safety composite system according to claim 1, wherein at least one film exhibits a cold crack temperature according to ISO 8570 of less than −35° C.

6. A safety composite system according to claim 1, at least one film exhibits a tensile impact strength according to DIN EN ISO 8256 of more than 2000 $kJ/m^2$.

7. A safety composite system according to claim 1, wherein at least one film exhibits an adhesion to a glass surface according to the compression shear test according to DIN 19 756 274 A1 of between 8 and 30 $N/mm^2$.

8. A safety composite system according to claim 1, wherein at least one film exhibits, in a thickness of d of 0.76 mm, an energy absorption E of at least 0.5 J/mm.

9. A safety composite system according to claim 1, wherein said composite system contains 2 to 10 transparent panels and 1 to 9 intermediate layer films.

10. A process for measuring the tensile impact strength of laminates of two transparent panels and a film arranged between the panels, said process comprising:
    breaking the transparent panels such that the edges of the fractures facing the intermediate layer do not exhibit any displacement vis-à-vis each other and for applying a defined energy by means of a tensile impact machine according to DIN ISO 8256 (2004).

11. A safety composite system according to claim 1, wherein and the constant b is −0.75 to 0.75.

12. A safety composite system according to claim 1, wherein the transparent panels are made of glass, polycarbonate or polymethyl methacrylate.

13. A safety composite system comprising: at least two transparent panels and at least one film based on partially acetalized polyvinyl alcohol which is arranged between the panels,
    wherein at least one film has a specific thickness-dependent energy absorption E [J/mm] of E>d−b determined on a test specimen consisting of the safety composite system provided with previously broken transparent panels according to DIN EN ISO 8256, the film thickness d amounting to 0.01 to 25 mm, the width of the test body to 14 mm and the constant b to 0.275 to −0.275, with the proviso that d=0.375 for film thicknesses of less 0.375 mm, and
    wherein at least one film consists of at least two partial films of crosslinked or non-crosslinked polyvinyl butyral with different plasticiser contents.

14. A safety composite system according to claim 13, wherein at least one film consists of several partial layers based on the materials of partially acetalized polyvinyl alcohol, PET, PU, PMMA and/or polyolefin.

15. A safety composite system according to claim 13, wherein at least one film is based on crosslinked or non-crosslinked plasticiser-containing polyvinyl butyral.

16. A safety composite system according to claim 13, wherein at least one film exhibits a cold crack temperature according to ISO 8570 of less than −35° C.

17. A safety composite system according to claim 13, at least one film exhibits a tensile impact strength according to DIN EN ISO 8256 of more than 2000 kJ/m².

18. A safety composite system according to claim 13, wherein at least one film exhibits an adhesion to a glass surface according to the compression shear test according to DIN 19 756 274 A1 of between 8 and 30 N/mm².

* * * * *